US00PP22000P3

(12) United States Plant Patent
van der Meer

(10) Patent No.: US PP22,000 P3
(45) Date of Patent: Jun. 28, 2011

(54) ***ECHINACEA* PLANT NAMED 'CATHARINA'**

(50) Latin Name: *Echinacea purpurea*
Varietal Denomination: Catharina

(76) Inventor: Cornelis van der Meer, Rijpwetering (NL)

( * ) Notice: Subject to any disclaimer, the term of this patent is extended or adjusted under 35 U.S.C. 154(b) by 0 days.

(21) Appl. No.: 12/589,198

(22) Filed: Oct. 19, 2009

(65) Prior Publication Data

US 2011/0093995 P1 Apr. 21, 2011

(51) Int. Cl.
*A01H 5/00* (2006.01)

(52) U.S. Cl. ..... Plt./428

(58) Field of Classification Search ..... Plt./428
See application file for complete search history.

*Primary Examiner* — June Hwu
*Assistant Examiner* — Louanne C Krawczewicz Myers

(57) ABSTRACT

A new and distinct *Echinacea purpurea* cultivar named 'CATHARINA' is disclosed, characterized by distinctive double dark pink flowers and uniquely strong peduncles. The new cultivar also have unique ray florets that resist drooping after harvest. The new variety is an *Echinacea*, and is normally used as a garden or container plant, and also suitable for cut flower production.

1 Drawing Sheet

Figure 1:
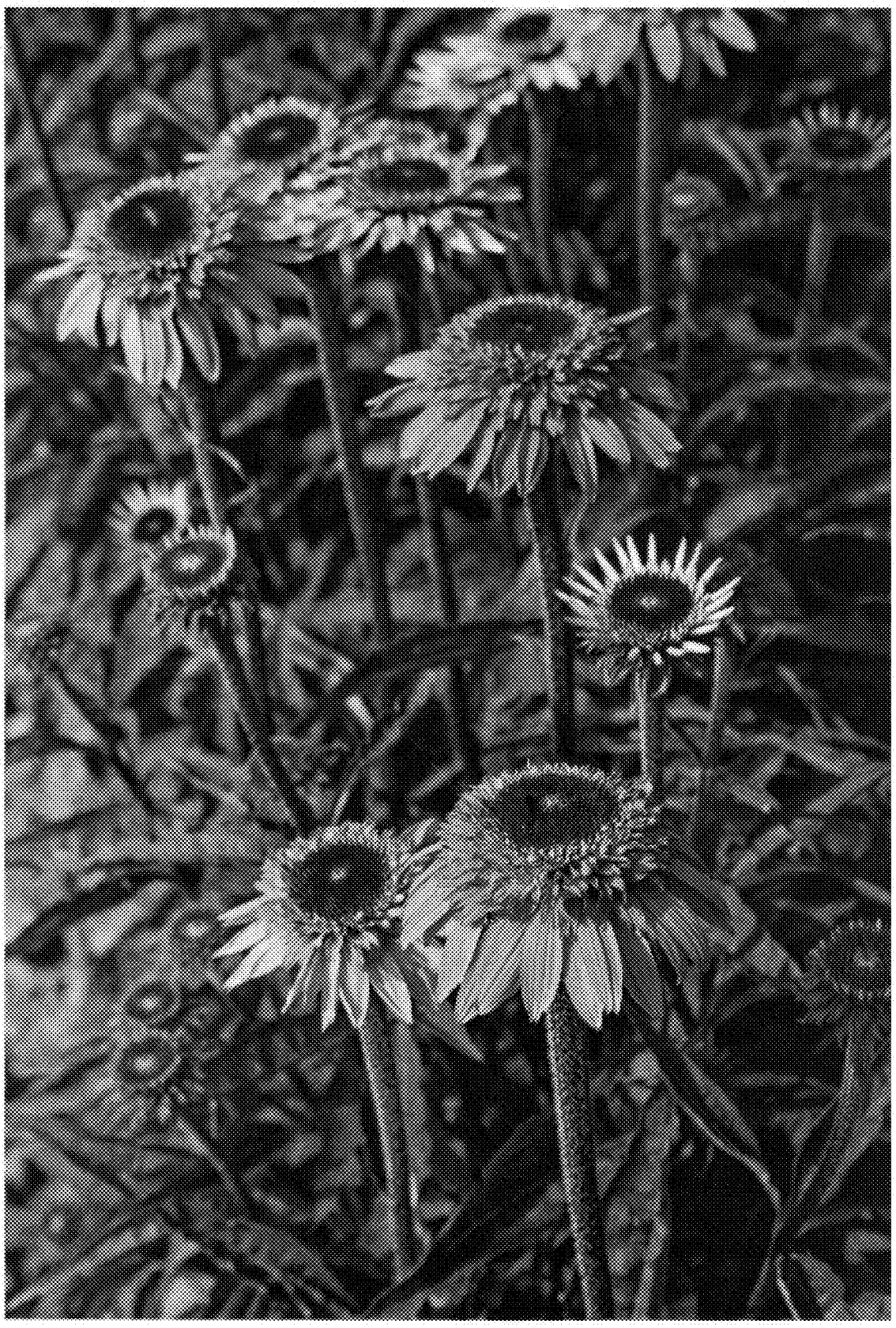

Latin name of the genus and species: *Echinacea purpurea.*
Variety denomination: 'CATHARINA'.

BACKGROUND OF THE INVENTION

The new cultivar was discovered as a chance, whole plant mutation in a commercial nursery in Rijpwetering, the Netherlands. The inventor, Cornelis Petrus van der Meer, a citizen the Netherlands, discovered the new variety as a naturally occurring whole plant mutation among several plants of the unpatented commercial variety, *Echinacea purpurea* 'Magnus'. The new variety was discovered in Spring of 2006 by the inventor.

Asexual reproduction of the new cultivar 'CATHARINA' by vegetative divisions was performed at a commercial nursery in Rijpwetering, the Netherlands in the Summer of 2006. Subsequently, reproduction has also been successful by tissue culture. Vegetative reproduction by tissue culture has produced several generations, and has shown that the unique features of this cultivar are stable and reproduced true to type through successive generations.

SUMMARY OF THE INVENTION

The cultivar 'CATHARINA' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'CATHARINA.' These characteristics in combination distinguish 'CATHARINA' as a new and distinct *Echinacea purpurea* cultivar:

1. Distinctive double dark pink flowers.
2. Uniquely strong peduncles.
3. Suitability for garden uses, and commercial cut flower production.
4. Durability of ray florets to resist drooping after harvest.

PARENT COMPARISON

Plants of the new cultivar 'Catharina' are similar to plants of the parent variety *Echinacea purpurea* 'Magnus' in most horticultural characteristics. However, plants of the new cultivar 'CATHARINA' produce double flowers, or a different color of pink. Additionally, ray florets of 'Magnus' will droop within a few days of harvesting flowers for cut flower purposes. Cut flowers of 'Catharina' will resist drooping ray florets for a minimum of 7 days.

COMMERCIAL COMPARISON

In addition to the parent variety, 'Catharina' can also be compared to the patented, commercially known variety *Echinacea purpurea* 'Pink Double Delight,' U.S. Plant Pat. No. 18,803. The new variety produces overall darker pink flowers, on a shorter plant. Additionally the ray florets of the new cultivar have a different shape, droop less and remain intact longer after harvesting a cut flower.

BRIEF DESCRIPTION OF THE PHOTOGRAPH

The accompanying photograph in FIG. 1 illustrates in full color a typical plant and flowers of 'CATHARINA' grown outdoors in Abbennes, the Netherlands. The plant has been growing in the ground for approximately 2 years. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'CATHARINA' plants grown outdoors in Abbennes, The Netherlands. Summer growing temperature ranged from approximately 14 to 33° C. during the day and 6 to 18° C. at night. Measurements and numerical values represent averages of typical flowering types. No chemical or photoperiodic treatments were given.

Botanical classification: *Echinacea purpurea* 'CATHARINA.'

PROPAGATION

Time to initiate rooting: 7 to 10 days at approximately 25° C.

Time to produce a young rooted liner: Approximately 40 days at approximately 22° C.

Root description: Fine, well-branched, fibrous, becoming slightly woody with age.

PLANT

Growth habit: Hardy, upright, herbaceous perennial.

Height: Approximately 58.4 cm.

Plant spread: Approximately 28.2 cm.

Growth rate: Moderate. Approximately 15 cm per months during Spring months, while actively growing.

Branching characteristics: Basal branching, moderately free branching.

Length of lateral branches: Approximately 23.8 cm, excluding inflorescence.

Diameter of lateral branches: Approximately 0.4 cm.

Quantity of lateral branches: Approximately 7.

Texture of lateral branches: Densely covered with short, strigose hairs. Average hair length approximately 0.05 cm. Hair color: Near RHS Green-White 157A.

Color of lateral branches: Near RHS Yellow-Green 146A.

Aspect: Approximately 25 angle from base of plant.

Strength of lateral branches: Very strong.

Internode length: Approximately 7.2 cm.

Age of plant described: Approximately 2 years old.

FOLIAGE

Leaf:

*Arrangement.*—Alternate, simple.

*Average length.*—Approximately 9.2 cm.

*Average width.*—Approximately 4.6 cm.

*Shape of blade.*—Narrowly ovate, slightly carinate.

*Apex.*—Acute to acuminate.

*Base.*—Attenuate.

*Attachment.*—Stalked.

*Margin.*—Sparsely serrate.

*Texture of top surface.*—Rough with a slightly glossy appearance. Densely covered with short strigose hairs. Average hair length approximately 0.03 cm, colored near RHS Green-White 157D.

*Texture of bottom surface.*—Rough with a slightly glossy appearance. Densely covered with short strigose hairs. Average hair length approximately 0.03 cm, colored near RHS Green-White 157D.

*Leaf internode length.*—Approximately 1.1 cm.

*Color.*—Young foliage upper side: Near RHS Green N137A. Young foliage under side: Near RHS Green 137B. Mature foliage upper side: Near RHS Green N137D Mature foliage under side: Near RHS Green 137B.

*Venation.*—Type: Pinnate. Venation color upper side: Near RHS Green 138C. Venation color under side: Near RHS Yellow-Green 144D.

Petiole:

*Length.*—Average 3.9 cm.

*Diameter.*—Approximately 0.3 cm.

*Texture.*—Glossy, smooth.

*Color.*—Near RHS Green 138B.

FLOWER

Bloom period: Naturally blooming continuously from Summer to mid-Fall. During this time, blooming begins approximately 20 weeks after planting a rooted liner.

Bud:

*Bud shape.*—Flattened globular.

*Bud length.*—Approximately 1.8 cm.

*Bud diameter.*—Approximately 2.8 cm.

*Bud color.*—Near Yellow-Green 145B. Center near Green 143A.

Inflorescence:

*Form.*—Terminal capitulum consisting of numerous disc florets, one row of ray florets and three rows of involucral bracts.

Flower:

*Diameter of entire flower.*—Approximately 6.8 cm.

*Depth of flower.*—Approximately 3.1 cm.

*Disc diameter.*—Approximately 4.4 cm.

*Receptacle shape.*—Flattened globular.

*Receptacle height.*—Average 1.0 cm.

*Receptacle diameter.*—Average 1.1 cm.

*Receptable color.*—Near RHS White N155B.

*Quantity of inflorescences per lateral stem.*—1.

*Quantity of open inflorescences and buds per plant.*—Average 7.

*Longevity.*—Average 5 weeks on the plant without significant fading or aging. Self-Cleaning.

*Fragrance.*—No fragrance.

Ray florets:

*Arrangement.*—Rotate.

*Aspect/orientation.*—Flat, approximately 120° angle from receptacle.

*Shape.*—Elliptic.

*Number of ray florets.*—Avg. 15.

*Length.*—Approximately 3.4 cm.

*Width.*—Approximately 1.1 cm.

*Apex shape.*—Emarginate.

*Base.*—Attenuate.

*Margin.*—Entire.

*Texture.*—Smooth, matte, moderately ribbed lengthwise.

*Color.*—Ray Florets Upper surface at first opening: Near RHS Red-Purple 70A. Upper surface at maturity: Near RHS Red-Purple 70B. Upper surface at fading: Not fading, color maintained. Under surface at first opening: Near RHS Red-Purple 61A, covered with a thin waxy appearing layer near Purple N77B. Under surface at maturity: Near RHS Red-Purple 70B covered with a thin waxy appearing layer near Purple N77B. Under surface at fading: Not fading, color maintained.

Disc florets:

*Number of disc florets.*—Approximately 500.

*Arrangement.*—Acropetally on disc.

*Length.*—Approximately 1.5 cm.

*Width.*—Approximately 0.4 cm.
*Shape.*—Tubular, lower ⅓ fused, upper ⅔ open.
*Margin.*—Entire.
*Apex.*—Acute.
*Base.*—Fused, acute.
*Texture.*—Smooth, glossy.
*Color disc florets.*—At first opening, only exterior visible: Near RHS Red-Purple 60B, base near Red-Purple 69C. At maturity, exterior surface: Near RHS Red-Purple 63C, tip near 63B base near Red-Purple 63D. At maturity, interior surface: Near RHS Red-Purple 61A.

Receptacle spines:
*Number of spines.*—Approximately 500.
*Length.*—Approximately 1 cm.
*Width.*—Approximately 0.1 cm.
*Spine shape.*—Acicular.
*Spine apex.*—Acute.
*Spine base.*—Attenuate.
*Spine texture.*—Smooth.
*Spine apex color.*—Near RHS Red-Purple 59A.
*Spine mid-section color.*—Near RHS Yellow-Green 144B.
*Spine base color.*—Near RHS Yellow-Green 145D.

Phyllaries/involucal bracts:
*Arrangement.*—Rotate, in 3 rows.
*Number.*—Approximately 75.
*Length.*—Approximately 0.9 cm.
*Width.*—Approximately 0.4 cm.
*Shape.*—Lanceolate.
*Apex.*—Acute.
*Base.*—Broadly cuneate.
*Margin.*—Entire.
*Texture.*—Sparsely pubescent near margins on both sides.
*Color.*—Inside color near RHS Green N137A. Outside color near RHS Green 137B.

PEDUNCLE

*Length.*—Average 15.8 cm.
*Width.*—Average 0.9 cm.
*Texture.*—Covered in strigose hairs.
*Color.*—Near RHS Yellow-Green 144A.
*Strength.*—Very strong.

REPRODUCTIVE ORGANS

Androecium:
Stamens not observed in any flowers to date.
Gynoecium: Present only disc florets.
*Pistil length.*—Approximately 0.9 cm.
*Stigma shape.*—Decurrent.
*Stigma color.*—Near RHS Greyed-Purple 187A.
*Style length.*—About 0.7 cm.
*Style color.*—Near RHS Green-White 157A.
*Ovary color.*—Near RHS Yellow-Green 145C.

OTHER CHARACTERISTICS

Disease resistance: Neither resistance nor susceptibility to diseases or pests normal to *Echinacea* have been observed in this variety.
Drought tolerance and temperature tolerance: Hardy perennial, low temperature tolerance to USDA Zone 4, at least. Tolerates high temperature extremely well, to at least 35° C. Some drought tolerance. Plants can be allowed in dry soil for several days without damage.
Fruit/seed production: Fruits and seeds have not been observed.

What is claimed is:

1. A new and distinct cultivar of *Echinacea* plant named 'CATHARINA' as herein illustrated and described.

* * * * *